(12) United States Patent
Suh et al.

(10) Patent No.: US 10,449,392 B2
(45) Date of Patent: Oct. 22, 2019

(54) RECTAL PHANTOM UNIT AND PHANTOM DEVICE INCLUDING THE SAME

(71) Applicant: THE CATHOLIC UNIVERSITY OF KOREA INDUSTRY-ACADEMIC COOPERATIVE FOUNDATION, Seoul (KR)

(72) Inventors: Tae Suk Suh, Seoul (KR); Ji Yeon Park, Seoul (KR); Seu Ran Lee, Seoul (KR); Jeong Woo Lee, Seoul (KR); Hae Jin Park, Suwon-si (KR); Kyoung Sik Choi, Anyang-si (KR)

(73) Assignee: THE CATHOLIC UNIVERSITY OF KOREA INDUSTRY-ACADEMIC COOPERATIVE FOUNDATION, Seoul (KR)

( * ) Notice: Subject to any disclaimer, the term of this patent is extended or adjusted under 35 U.S.C. 154(b) by 202 days.

(21) Appl. No.: 15/548,679

(22) PCT Filed: Apr. 2, 2015

(86) PCT No.: PCT/KR2015/003332
§ 371 (c)(1),
(2) Date: Aug. 30, 2017

(87) PCT Pub. No.: WO2016/125948
PCT Pub. Date: Aug. 11, 2016

(65) Prior Publication Data
US 2018/0036555 A1    Feb. 8, 2018

(30) Foreign Application Priority Data
Feb. 4, 2015    (KR) .................. 10-2015-0017623

(51) Int. Cl.
*A61N 5/10* (2006.01)
*A61B 90/17* (2016.01)
*A61B 18/00* (2006.01)

(52) U.S. Cl.
CPC ............ *A61N 5/1075* (2013.01); *A61B 90/17* (2016.02); *A61N 5/10* (2013.01); *A61N 5/1071* (2013.01);
(Continued)

(58) Field of Classification Search
CPC .......... A61N 2005/1076; A61N 5/1071; A61N 5/1075; A61B 2018/005
See application file for complete search history.

(56) References Cited

U.S. PATENT DOCUMENTS

2005/0141672 A1    6/2005    Endo et al.

FOREIGN PATENT DOCUMENTS

KR    10-2008-0006142 A    1/2008
KR    10-2009-0013894 A    2/2009
(Continued)

OTHER PUBLICATIONS

International Search Report for PCT/KR2015/003332, dated Oct. 1, 2015.

*Primary Examiner* — Christine H Matthews
(74) *Attorney, Agent, or Firm* — Novick, Kim & Lee, PLLC; Sang Ho Lee (57) ABSTRACT

An aspect of the present invention provides a rectal phantom unit and a phantom device including the same, including: a holder having a penetration portion formed in a longitudinal direction thereof; a rectal simulant which is inserted to the penetration portion of the holder, includes a plurality of unit plates laminated thereon, and simulates a rectum of a body; and a film which is disposed between the rectal simulant and (Continued)

the holder and measures an absorbed dose of radiation irradiated to the rectal simulant.

8 Claims, 7 Drawing Sheets (52) U.S. Cl.
CPC ............... *A61B 2018/005* (2013.01); *A61B 2018/00547* (2013.01); *A61N 2005/1076* (2013.01); *A61N 2005/1094* (2013.01); *A61N 2005/1097* (2013.01)

(56) References Cited

FOREIGN PATENT DOCUMENTS

| | | |
|---|---|---|
| KR | 10-2012-0079726 A | 7/2012 |
| KR | 10-2012-0087477 A | 8/2012 |
| KR | 10-2012-0100289 A | 9/2012 |

RECTAL PHANTOM UNIT AND PHANTOM DEVICE INCLUDING THE SAME

CROSS REFERENCE TO RELATED APPLICATIONS

This application is a National Stage of International Application No. PCT/KR2015/003332 filed Apr. 2, 2015, claiming priority based on Korean Patent Application No. 10-2015-0017623 filed Feb. 4, 2015, the contents of all of which are incorporated herein in their entireties by reference.

TECHNICAL FIELD

The present invention relates to a rectal phantom unit and a phantom device including the same. More particularly, the present invention relates to a rectal phantom unit and a phantom device including the same that enables safe and effective radiotherapy by verifying an absorbed dose delivered to a rectal wall by simulating a patient's rectum according to the use of a rectal balloon during radiotherapy.

BACKGROUND ART

Radiotherapy is used for treating cancer or reducing a patient's pain by killing or no longer proliferating cancer cell so that the cancer cells die due to the end of the lifetime.

Such radiotherapy is performed, for example, for preventing recurrence when there is a large possibility that the cancer cells remain after surgery, a case where the surgery cannot be performed, a case where radiotherapy is more effective than the surgery, a case of enhancing the quality of the patient's life in combination of surgery and radiotherapy, or minimizing an anti-cancer effect in combination of anti-cancer chemotherapy.

The radiotherapy is performed by a medical device including a radiation generator such as a linear accelerator. The linear accelerators has been used as a current standard device for radiotherapy by outputting high energy X-rays or electron beams and finely adjusting an output radiation dose.

It is necessary to control appropriately a radiation dose output from a radiotherapy device when the radiotherapy is performed. The best treatment effect may be obtained by irradiating an optimal dose of radiation corresponding to a condition, size or depth of the tumor and an effect on other organs adjacent to an organ with the tumor (for example, a phenomenon in which the rectum adjacent to the prostate is damaged by radiation during treatment of prostate cancer), and thus, it is very important to form an optimal dose distribution by irradiating radiation of the linear accelerator.

As a result, before using a radiotherapy device, it is necessary to confirm in advance operational precision such as whether the accelerator operates properly, especially whether a planned radiation dose is transmitted by normally controlling the radiation dose. In addition, it is preferred that the operation of the linear accelerator and the radiation does measure an absorbed dose delivered to a specific part in the body of the patient to be actually treated. The thing used for this purpose is called a phantom in the medical field and a measurement device made to measure the radiation instead of the body.

On the other hand, it is preferable to minimize a radiation exposure dose to the rectum while simultaneously delivering a maximum radiation dose to the tumor, in order to prevent the rectum as a main protective organ from being damaged by the radiation during treatment of prostate cancer. Therefore, for effective treatment, it is necessary to predict a dose value delivered to the patient before radiotherapy, particularly, a dose distribution delivered to the tumor and the rectum. As a result, there is a need for a rectal phantom capable of verifying the accuracy of the dose distribution delivered to the rectum during radiotherapy of the prostate by simulating the rectum of the patient.

DISCLOSURE

Technical Problem

An object of the present invention is to provide a rectal phantom unit and a phantom device including the same that enables safe and effective radiotherapy by verifying an absorbed dose delivered to a rectal wall by simulating a patient's rectum according to the use of a rectal balloon during radiotherapy.

Technical Solution

An aspect of the present invention provides a rectal phantom unit including a holder having a penetration portion formed in a longitudinal direction thereof; a rectal simulant which is inserted to the penetration portion of the holder, includes a plurality of unit plates laminated thereon, and simulates a rectum of a body; and a film which is disposed between the rectal simulant and the holder and measures an absorbed dose of radiation irradiated to the rectal simulant.

A film seating portion formed to be stepped so that the film is seated may be included on the outer surface of the rectal simulant or the inner surface of the holder.

Glass dosimeters for measuring a radiation dose irradiated to the rectal simulant may be inserted into the unit plates.

The rectal simulant may have a cylindrical shape, a plurality of glass dosimeters may be included, and the plurality of glass dosimeters may be arranged so that angles between the adjacent glass dosimeters are equal to or larger than 45° based on the central axis of the rectal simulant.

The rectal simulant may further include intermediate plates provided between the adjacent unit plates so as to separate the glass dosimeters from each other.

In the rectal simulant, a balloon insertion portion to which a rectal balloon for fixing the prostate is inserted may be formed by passing through the unit plates.

A film that measures the dose of radiation irradiated to the inner surface of the rectal simulant may be provided on the inner surface of the rectal simulant.

Another aspect of the present invention provides a phantom device for measuring distribution of radiation irradiated to a rectum of a body, the phantom device including: a lower abdomen simulant having an insertion hole formed at one surface and simulating the lower abdomen of the body; and a rectal phantom unit inserted to the insertion hole.

Advantageous Effects

According to the exemplary embodiment of the present invention, safe and effective radiotherapy is enabled by verifying an absorbed dose delivered to a rectal wall by simulating a patient's rectum according to the use of a rectal balloon during radiotherapy.

MODES OF THE INVENTION

The present invention may have various modifications and various exemplary embodiments and specific exemplary embodiments will be described in detail in the detailed description. However, this does not limit the present invention to specific exemplary embodiments, and it should be understood that the present invention covers all the modifications, equivalents and replacements included within the idea and technical scope of the present invention. In describing the present invention, when it is determined that the detailed description of the publicly known art related to the present invention may obscure the gist of the present invention, the detailed description thereof will be omitted.

Hereinafter, a rectal phantom unit and a phantom device including the same of the present invention will be described in detail with reference to the accompanying drawings, and in the description with reference to the accompanying drawings, like or corresponding components designate like reference numerals, and a duplicate description thereof will be omitted.

Figure 1:
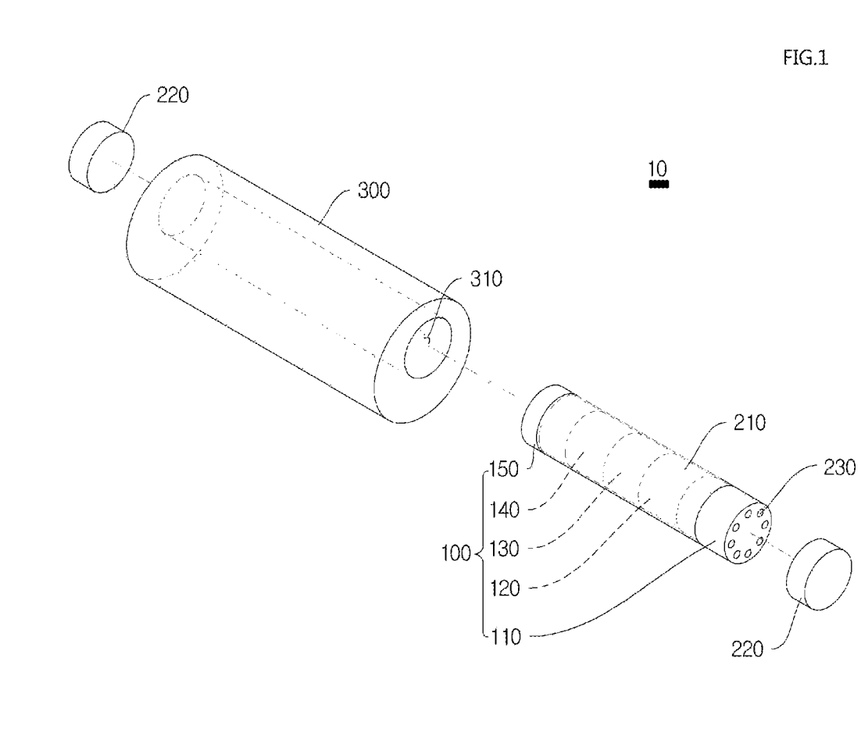
FIG. 1 is a schematic diagram of a rectal phantom unit according to an exemplary embodiment of the present invention.

FIG. 1 is a schematic diagram of a rectal phantom unit 10 according to an exemplary embodiment of the present invention, and in FIG. 1, a rectal simulant 100, unit plates 110, 120, 130, 140, and 150, a film 210, a holder 300, and a penetration portion 310 are illustrated.

The rectal phantom unit 10 according to the exemplary embodiment includes the holder having the penetration portion 310 formed in a longitudinal direction, the rectal simulant 100 which is inserted to the penetration portion 310 of the holder 300, includes a plurality of unit plates 110, 120, 130, 140, and 150 laminated thereon, and simulates a rectum of a body, and the film 210 which is disposed between the rectal simulant 100 and the holder 300 and measures an absorbed dose of radiation irradiated to the rectal simulant 100, thereby enabling accurate prediction of a dose distribution of radiation irradiated to the rectum during radiotherapy and safe and effective radiotherapy of the prostate.

The holder 300 has the penetration portion 310 formed in the longitudinal direction and fixes the unit plates 110, 120, 130, 140, and 150 and the film 210 to be described later. The rectal simulant 100 is inserted to the penetration portion 310 and the penetration portion 310 may be eccentrically formed in the holder 300 by considering a position of the rectum of the body. In this case, the holder 300 may be made of an acryl material. Acryl is a material equivalent with the tissue of the body and does not affect the dose measurement during irradiation of radiation.

The rectal simulant 100 simulating the rectum of the body is formed by laminating the plurality of unit plates 110, 120, 130, 140, and 150 and inserted to the penetration portion 310 of the holder 100. The plurality of unit plates 110, 120, 130, 140, and 150 are laminated along the length of the patient's rectal wall and the outer surface of the unit plates 110, 120, 130, 140 and 150 is formed to correspond to the inner surface of the holder 300.

The film 210 is provided between the rectal simulant 100 and the holder 300 to measure the dose and distribution of radiation irradiated to the rectal simulant 100. That is, the dose and distribution of radiation irradiated to the rectal wall may be predicted using the film 210 provided on the outer surface of the rectal simulant 100. The film 210 may be provided between the rectal simulant 100 and the holder 300 to fit without being spaced apart from each other. When an air layer is formed between the film 210 and the unit plates 110, 120, 130, 140 and 150 or between the film 210 and the holder 300, an electron disturbance phenomenon occurs due to a difference in density while the irradiated radiation passes through the air layer and thus, it is difficult to accurately measure the dose.

After the rectal simulant 100 is inserted to the holder 300, a holder cap 220 may be inserted to both ends of the penetration portion 310. The holder cap 220 fixes the rectal simulant 100 into the holder 300. The holder cap 220 may be made of an acryl material. In the exemplary embodiment, the case where the rectal simulant 100 is fixed into the holder 300 by the holder cap 220 is mainly described, but a female screw portion (not illustrated) is formed at the end of a hollow portion 310 of the holder 300 and a male screw portion (not illustrated) corresponding to the female screw portion is formed on the unit plates 110 and 150 located at both ends of the hollow portion 310 to fix the rectal simulant 100 into the holder 300 by screw coupling.

Figure 2:
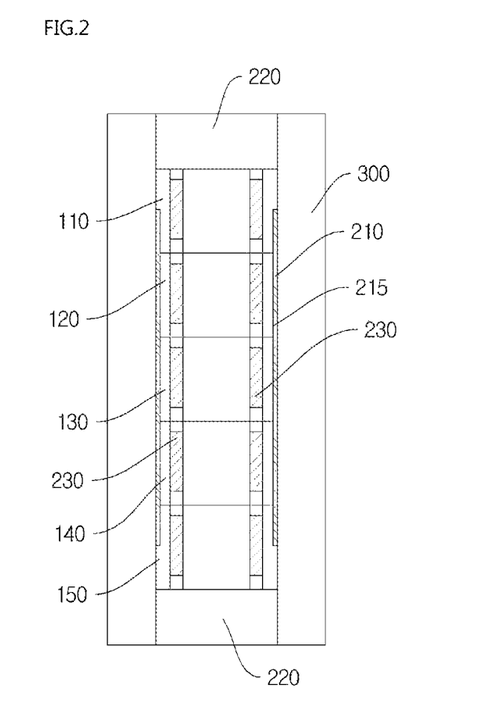
FIGS. 2 and 3 are a cross-sectional view and a plan view of a rectal phantom unit according to a modification of the exemplary embodiment of the present invention.

On the other hand, a film seating portion 215 formed to be stepped so that the film 210 is seated may be included on the outer surface of the rectal simulant 100 or the inner surface of the holder 300. Referring to FIG. 2, the film seating portion 215 is formed on the inner surface of the rectal simulant 100 and the film 210 for measuring the radiation distribution is provided. The height of the step of the film seating portion 215 is formed to be equal to the thickness of the film 210 to prevent the air layer from being formed between the film 210 and the inner surface of the holder 300 when the rectal simulant 100 is inserted into the holder 300.

In the exemplary embodiment, the case where the film seating portion 215 is formed on the outer surface of the rectal simulant 100 and the film 210 is seated on the film seating portion 215 is mainly described, but the film seating portion 215 may be formed on the inner surface of the holder 300 and the film 210 may be seated on the film seating portion 215.

Figure 3:
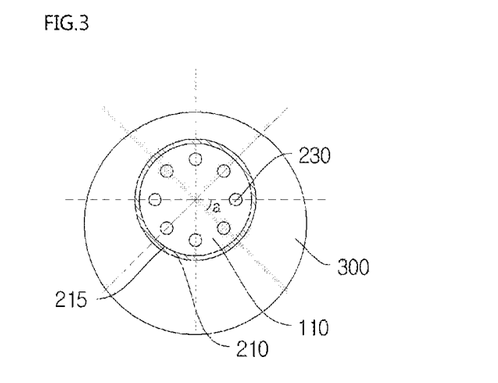
Figure 4:
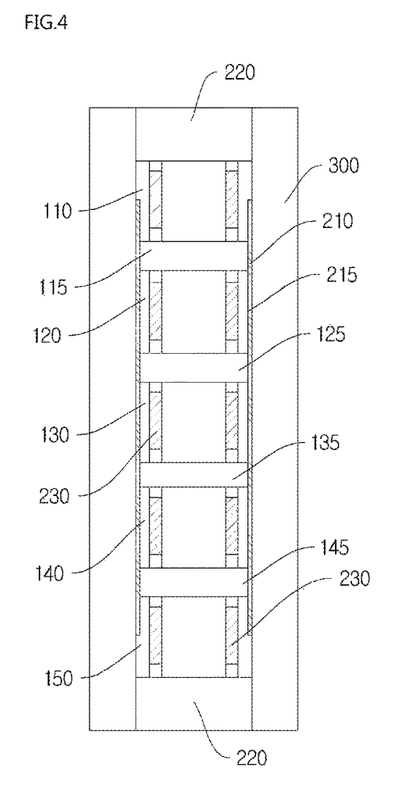
FIG. 4 is a cross-sectional view of a rectal phantom unit according to another modification of the exemplary embodiment of the present invention.

FIGS. 2 and 3 are a cross-sectional view and a plan view of a rectal phantom unit 10 according to a modification of the exemplary embodiment of the present invention and FIG. 4 is a cross-sectional view of a rectal phantom unit 10 according to another modification of the exemplary embodiment of the present invention.

In FIGS. 2 to 4, a rectal simulant 100, unit plates 110, 120, 130, 140, and 150, intermediate plates 115, 125, 135, and 145, a film 210, a film seating portion 215, a holder cap 220, a glass dosimeter 230, and a holder 300 are illustrated.

Since the rectal phantom unit 10 according to the exemplary embodiment is the same as the rectal phantom unit 10 according the previous exemplary embodiment except for the configurations of the glass dosimeter 230 and the intermediate plates 115, 125, 135, and 145, the description of the same configurations will be replaced with the description of the previous exemplary embodiment.

The glass dosimeter 230 for measuring a radiation dose irradiated to the rectal simulant 100 may be inserted into the unit plates 110, 120, 130, 140, and 150 forming the rectal simulant 100. The glass dosimeter 230 may be provided to be inserted to holes (not illustrated) formed in the unit plates 110, 120, 130, 140, and 150. The glass dosimeter 230 has an advantage that a measured value may be read repeatedly even if a mistake occurs in a reading process because excited electrons do not fall to the ground state and return to a specific energy level.

In FIGS. 2 and 4, it is illustrated that the glass dosimeter 230 is inserted to all of the unit plates 110, 120, 130, 140, and 150, but the glass dosimeter 230 may be inserted to some of the unit plates 110, 120, 130, 140, and 150 depending on a measurer's selection to measure the dose of radiation at a desired position.

Meanwhile, the rectal simulant 100 may have a cylindrical shape and a plurality of glass dosimeters 230 are included, and the plurality of glass dosimeters 230 may be arranged so that angles between the adjacent glass dosimeters 230 are equal to or larger than 45° based on the central axis of the rectal simulant 100.

Referring to FIG. 3, the glass dosimeters 230 are annularly arranged on the outer side of the unit plate 110 and the angles between the adjacent glass dosimeters 230 may be 45° or more. When an angle a between the adjacent glass dosimeters 230 is less than 45°, one glass dosimeter 230 may affect other glass dosimeters 230 therearound to interfere with accurate dose measurement.

Meanwhile, the rectal simulant 100 may further include the intermediate plates 115, 125, 135, and 145 provided between the adjacent unit plates 110, 120, 130, 140, and 150 so as to separate the glass dosimeters 230 from each other. The intermediate plates 115, 125, 135, and 145 have the same cross-sectional areas as the unit plates 110, 120, 130, 140, and 150 and are provided between the unit plates 110, 120, 130, 140, and 150. The intermediate plates 115, 125, 135, and 145 separate the glass dosimeters 230 provided in the unit plates 110, 120, 130, 140, and 150 from each other to prevent one glass dosimeter 230 from affecting other glass dosimeters 230 vertically adjacent to each other. The intermediate plates 115, 125, 135, and 145 may be formed to have a height of 5 to 7 mm by considering interference between the glass dosimeters 230. Meanwhile, in the exemplary embodiment, the case where the unit plates 110, 120, 130, 140 and 150 and the intermediate plates 115, 125, 135 and 145 are sequentially laminated is exemplified, but the arrangement and the positions of the glass dosimeters 230 may be varied in the rectal phantom unit 10.

According to the exemplary embodiment, the dose and distribution of the radiation irradiated to the rectal outer wall may be predicted using the film 210 provided on the outer surface of the rectal simulant 100, and the dose of radiation irradiated into the rectal wall may be predicted using the glass dosimeters 230 inserted to the unit plates 110, 120, 130, 140 and 150.

Meanwhile, in the exemplary embodiment, the case where the film 210 and the glass dosimeters 230 are used at the same time to predict the dose of radiation is mainly described, but if necessary, the film 210 or the glass dosimeter 230 may be selected to measure the dose of radiation. At this time, in case of predicting the radiation dose using only the film 210, an acrylic rod (not illustrated) having the same diameter and height as the glass dosimeter 230 is inserted into an insertion hole (not illustrated) into which the glass dosimeter 230 is inserted to block the insertion hole (not illustrated) and then measure the radiation dose. Further, in the case of predicting the radiation dose using only the glass dosimeter 230, it is also possible to measure the radiation dose by using the rectal simulant 100 in which the film seating portion 215 is not formed.

Figure 5:
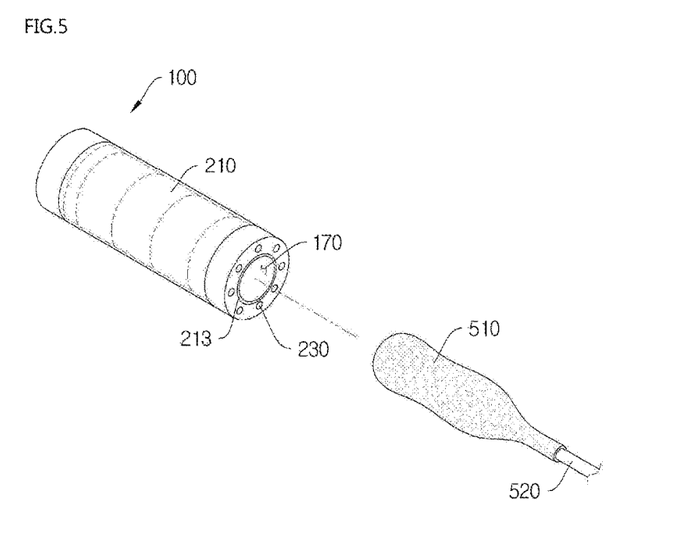
FIGS. 5 and 6 are perspective views of a rectal phantom unit according to another exemplary embodiment of the present invention.
Figure 6:
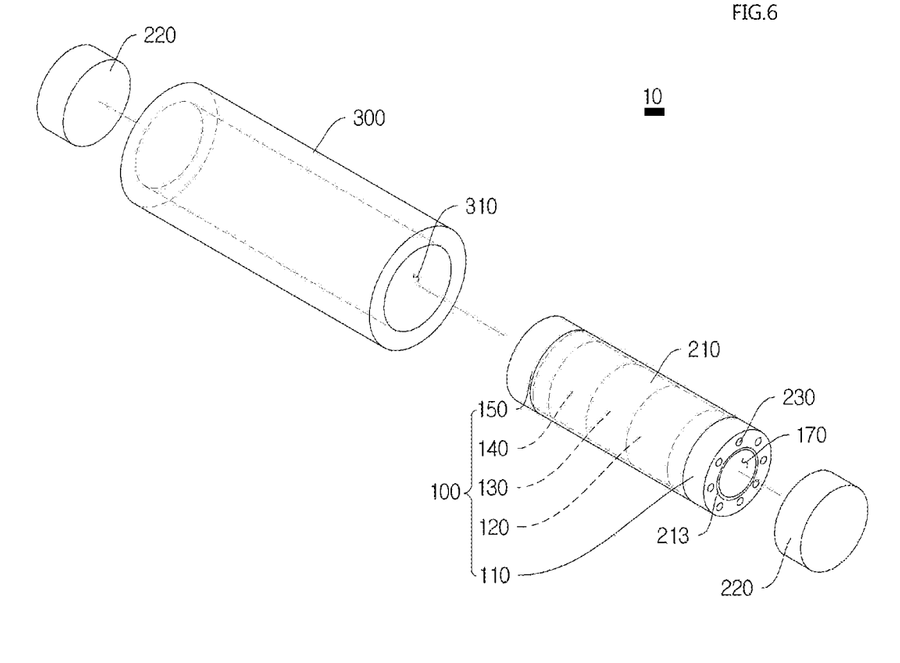

FIGS. 5 and 6 are perspective views of a rectal phantom unit 10 according to another exemplary embodiment of the present invention.

In FIGS. 5 and 6, a rectal simulant 100, a balloon insertion portion 170, films 210 and 213, a holder 300, a penetration portion 310, a rectal balloon 510, and an air injection portion 520 are illustrated.

Since the rectal simulant 100 in the rectal phantom unit 10 according to the exemplary embodiment is the same as rectal simulant 100 in the rectal phantom unit 10 according to the previous exemplary embodiment, like configurations will be replaced with the description of the previous exemplary embodiment.

In the rectal simulant 100, the balloon insertion portion 170 to which the rectal balloon 510 for fixing the prostate is inserted may be formed by passing through the unit plates 110, 120, 130, 140 and 150.

Generally, the rectal balloon 510 may be used to fix the motion of the prostate during radiotherapy of prostate cancer and expand the rectum using a balloon effect so that only a part of the rectal wall is exposed to radiation, thereby minimizing the exposure dose of the rectal wall. The rectal balloon 510 inflates the rectum with a constant shape and volume by inserting the balloon into the rectum, fixing the balloon, and then injecting air through the air injection unit 520 connected to the balloon end. When the rectum is inflated, the dose of absorbed radiation per unit area is reduced compared to when the rectum is not inflated, thereby reducing the damage of the rectum by radiation.

However, since the inside of the rectal balloon 510 includes air having a density lower than that of the body, when the irradiated radiation passes through the rectum and rectal balloon 510, an electromagnetic disturbance due to a nonuniform material composition occurs, and thus, it is difficult to predict the accurate dose. In addition, nonuniform secondary dose increase and dose deficiencies may occur at the boundary between two materials with a large difference in density. Accordingly, it is necessary to verify that how air inside the rectal balloon 510 has a dose effect on the irradiated radiation and the rectal wall when the rectal balloon 510 is inserted into the rectum. Further, it is also necessary to evaluate whether the use of the rectal balloon 510 is clinically effective for radiotherapy as compared to the case where the rectal balloon 510 is not used.

In the exemplary embodiment, by simulating the case where the air is injected after the rectal balloon 510 is inserted using the balloon insertion portion 170 formed in the rectal simulant 100 to inflate the rectum, how the rectal balloon 510 inserted to the rectum of the body has an effect on the dose measurement and an effect of the use of the rectal balloon 510 during radiotherapy may be evaluated.

Referring to FIG. 6, the penetration portion 310 is formed in the holder 300 in a longitudinal direction and the penetration portion 310 may be formed at the center of the holder 30 by considering the position of the rectum of the body when the rectal balloon 510 is inserted to the rectum.

On the other hand, a film 213 that measures a dose of radiation irradiated to the inner surface of the rectal simulant 100 may be provided on the inner surface of the rectal simulant 100. The film 213 is in a close contact with the inner surface of the rectal simulant 100 formed by the balloon insertion portion 170 so that an air layer is not formed.

It is possible to predict the dose and distribution of the radiation irradiated to the rectal outer wall using the film 210 provided on the outer surface of the rectal simulant 100 and predict the dose and distribution of the radiation irradiated to the rectal inner wall using the film 213 provided on the inner surface of the rectal simulant 100.

Figure 7:
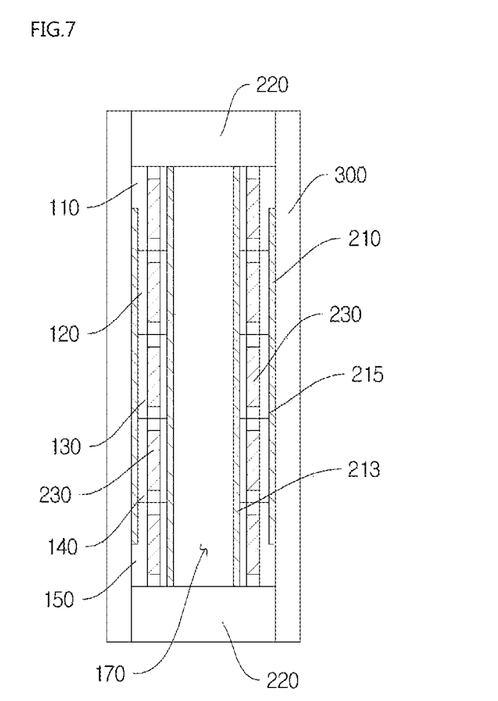
FIGS. 7 and 8 are a cross-sectional view and a plan view of a rectal phantom unit according to a modification of another exemplary embodiment of the present invention.
Figure 8:
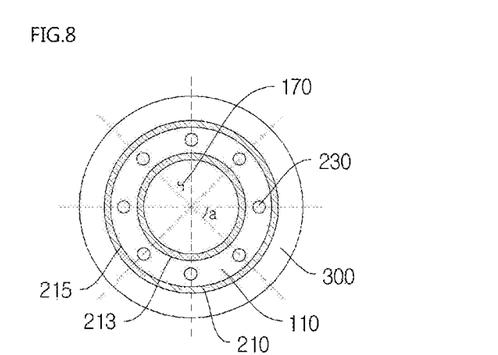
Figure 9:
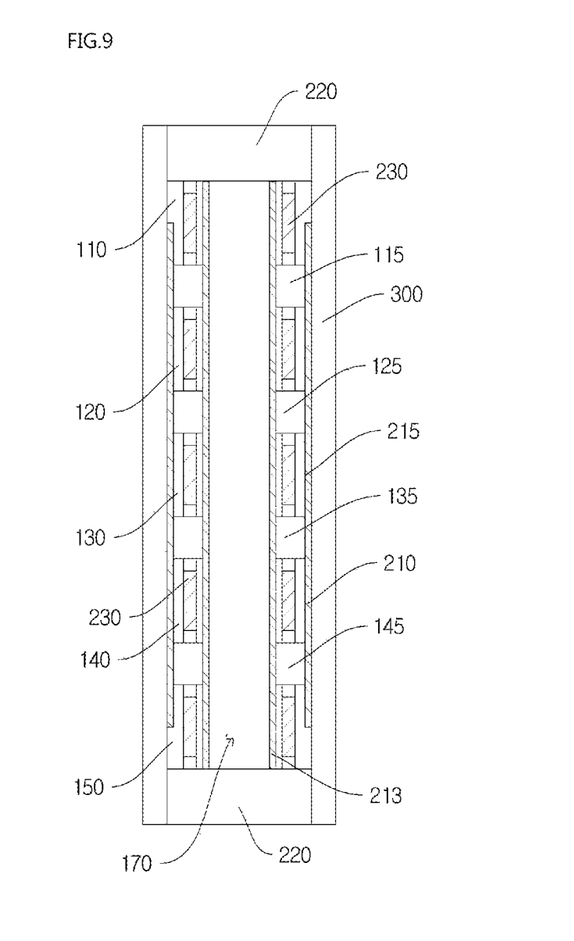
FIG. 9 is a cross-sectional view of a rectal phantom unit according to another modification of another exemplary embodiment of the present invention.

FIGS. 7 and 8 are a cross-sectional view and a plan view of a rectal phantom unit according to a modification of another exemplary embodiment of the present invention and FIG. 9 is a cross-sectional view of a rectal phantom unit according to another modification of another exemplary embodiment of the present invention.

Since the rectal phantom unit according to the exemplary embodiment is the same as the rectal simulant 100 of the rectal phantom unit 100 according to the previous exemplary embodiment described in FIGS. 2 to 4 except for the configuration of the balloon insertion portion 170 to which the rectal balloon 510 is inserted and the film 213 provided on the inner surface of the rectal simulant 100, like configurations will be replaced with the description of the previous exemplary embodiment.

The rectal balloon 510 is inserted into the balloon inserting section 170 and the film 213 is provided on the inner surface of the rectal simulant 100 to measure a dose of radiation radiated to the inner surface of the rectal simulant 100. Meanwhile, the intermediate plates 115, 125, 135 and 145 provided between the unit plates 110, 120, 130, 140 and 150 correspond to the shapes of the unit plates 110, 120, 130, 140 and 150 to form the balloon insertion portion 170.

Figure 10:
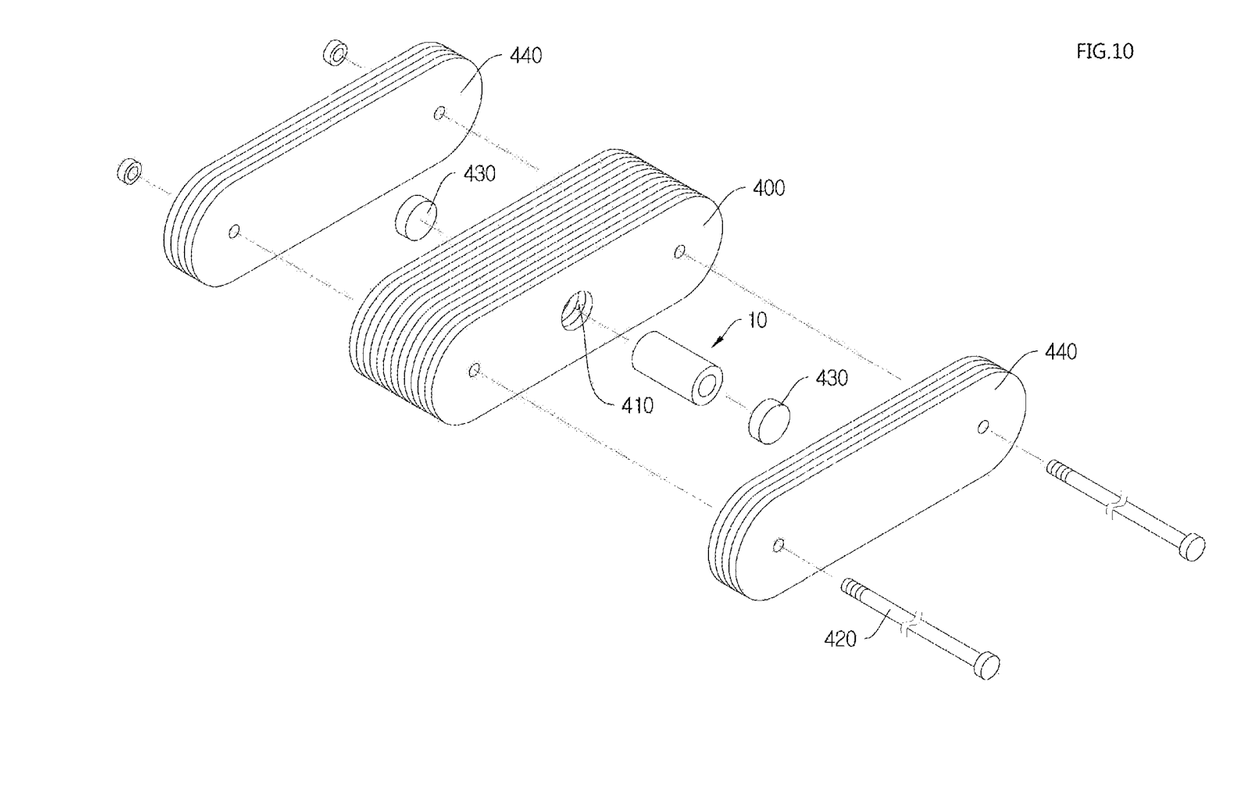
FIG. 10 is a schematic diagram of a phantom device including the rectal phantom unit according to the present invention.

FIG. 10 is a schematic diagram of a phantom device including the rectal phantom unit according to the present invention. Referring to FIG. 10, a rectal phantom unit 10, a lower abdomen simulant 400, an insertion hole 410, a lower abdomen simulant cap 430, a coupler 420, and a cover plate 440 are illustrated.

The phantom device according to the exemplary embodiment includes a lower abdomen simulant 400 having an insertion hole 410 formed at one surface and simulating the lower abdomen of the body and a rectal phantom unit 10 inserted to the insertion hole 410 in a phantom device for measuring a distribution of radiation irradiated to the rectum of the body.

Since the rectal phantom unit 10 of the phantom device according to the exemplary embodiment is the same as the configuration of the rectal phantom unit 10 of the previous exemplary embodiment, like configurations will be replaced with the description of the previous exemplary embodiment.

The lower abdomen simulant 400 simulates the lower abdomen of the body by laminating a plurality of plates and may be made of an acryl material. The cover plate 440 is provided before/after the lower abdomen simulant 400 to cover the lower abdomen simulant 400. The lower abdomen simulant 400 and the cover plate 440 are fastened to each other by the coupler 420. In the exemplary embodiment, the coupler 420 refers to a means that fastens and fixes a plurality of objects to each other and may be fixed by a screw coupling of a bolt and a nut as illustrated in FIG. 10. It is preferred that the coupler 420 is made of an equivalent material with the tissue of the body such as acrylic by considering an effect on the dose measurement when the radiation is irradiated.

The insertion hole 410 is formed at the center of the lower abdomen simulant 400 to penetrate in a longitudinal direction and the rectal phantom unit 10 is inserted into the insertion hole 410. The lower abdomen simulant cap 430 is inserted into both ends of the insertion hole 410 to fix the rectal phantom unit 10 inserted into the lower abdomen simulant 400.

The cover plate 440 is for simulating the tissue around the rectum, and covers the lower abdomen simulant 400 to provide an electron equilibrium state to a measured site, thereby providing more accurate and stable measurement conditions. That is, the cover plate 440 is disposed before/after the lower abdomen simulant 400 in the longitudinal direction of the rectal phantom unit 10 to prevent direct exposure to radiation during irradiation of radiation, thereby forming conditions capable of measuring the dose stably and accurately by the rectal phantom unit 10.

As described above, it is possible to precisely simulate the condition of the rectum of the body by using the lower abdomen simulant 400 and the rectal phantom unit 10 and to more accurately measure and predict the dose and distribution of the radiation irradiated to the rectum during the treatment of prostate cancer.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

The invention claimed is:

1. A rectal phantom unit, comprising: a holder having a penetration portion formed in a longitudinal direction;
   a rectal simulant which is inserted into the penetration portion of the holder, the rectal simulant including a plurality of unit plates laminated thereon, and simulating a rectum of a body; and
   a film which is disposed between the rectal simulant and the holder and measures an absorbed dose of radiation irradiated to the rectal simulant.

2. The rectal phantom unit of claim 1, wherein on an outer surface of the rectal simulant or an inner surface of the holder, a film seating portion is stepped so that the film is seated.

3. The rectal phantom unit of claim 1, wherein
   glass dosimeters for measuring a radiation dose irradiated to the rectal simulant are inserted into the unit plates.

4. The rectal phantom unit of claim 3, wherein the rectal simulant has a cylindrical shape, the plurality of glass dosimeters are included, and the plurality of glass dosimeters are arranged so that angles between the glass dosimeters are equal to or larger than 45° based on a central axis of the rectal simulant.

5. The rectal phantom unit of claim 3, wherein the rectal simulant further includes intermediate plates provided between the unit plates so as to separate the glass dosimeters from each other.

6. The rectal phantom unit of claim 1, wherein the rectal simulant comprises, a balloon insertion portion to which a rectal balloon for fixing a prostate is inserted by passing through the unit plates.

7. The rectal phantom unit of claim 6, wherein on an inner surface of the rectal simulant, an additional film that measures a dose of radiation irradiated to the inner surface of the rectal simulant is provided.

8. A phantom device for measuring distribution of radiation irradiated to a rectum of a body, the phantom device comprising:

a lower abdomen simulant having an insertion hole formed at one surface and simulating a lower abdomen of the body; and a rectal phantom unit inserted to the insertion hole according to claim 1.

\* \* \* \* \*